United States Patent [19]

McClean et al.

[11] Patent Number: 4,881,177

[45] Date of Patent: Nov. 14, 1989

[54] ULTRASONIC SCANNING SYSTEM

[75] Inventors: James H. McClean, Belfast; Neil A. Campbell, County Down; Iain M. Reid, Belfast, all of Northern Ireland

[73] Assignee: Short Brothers PLC, Belfast, Northern Ireland

[21] Appl. No.: 863,413

[22] PCT Filed: Sep. 9, 1985

[86] PCT No.: PCT/GB85/00405

§ 371 Date: Apr. 28, 1986

§ 102(e) Date: Apr. 28, 1986

[87] PCT Pub. No.: WO86/01897

PCT Pub. Date: Mar. 27, 1986

[30] Foreign Application Priority Data

Sep. 12, 1984 [GB] United Kingdom ............... 8423023

[51] Int. Cl.$^4$ ........................................... G01B 7/34
[52] U.S. Cl. .................................... 364/513; 73/619; 73/634; 364/474.37; 901/44; 901/47
[58] Field of Search ............... 364/513, 167, 191–193, 364/474.37, 507; 73/634, 637, 638, 640, 619, 621; 901/44, 46, 47

[56] References Cited

U.S. PATENT DOCUMENTS

| | | | |
|---|---|---|---|
| 3,534,396 | 10/1970 | Hast et al. | 364/474 |
| 3,898,838 | 8/1975 | Connelly | 73/634 |
| 4,117,539 | 9/1978 | Bell et al. | 364/507 |
| 4,213,183 | 7/1980 | Bamon et al. | 364/507 |
| 4,311,556 | 1/1982 | Iwanoto et al. | 901/46 |
| 4,311,652 | 1/1982 | Jeffras et al. | 73/634 |
| 4,355,447 | 10/1982 | DiMatteo et al. | 364/474 |
| 4,370,889 | 2/1983 | Ruthrof et al. | 73/619 |
| 4,379,335 | 4/1983 | Kirsch | 364/513 |
| 4,385,360 | 5/1983 | Yamada et al. | 364/475 |
| 4,393,450 | 7/1983 | Jerard et al. | 364/474 |
| 4,434,660 | 3/1984 | Michaels et al. | 73/637 |
| 4,470,122 | 9/1984 | Sam | 364/507 |
| 4,495,587 | 1/1985 | Plante et al. | 364/507 |
| 4,531,192 | 7/1985 | Cook | 364/513 |
| 4,618,934 | 10/1986 | Nagase | 364/507 |
| 4,653,011 | 3/1987 | Iwano | 901/44 |
| 4,663,727 | 5/1987 | Saporito et al. | 73/638 |

FOREIGN PATENT DOCUMENTS 2132353 7/1984 United Kingdom .

OTHER PUBLICATIONS

Davidenko et al.: "Making Ultrasonic Inspection of Welded Joints More Efficient by Means of Cybernetics", Apr. 1980, pp. 29–35, Automatic Welding V. 33, No. 4.

Rogers, et al., "A Simple CADCAM System for the Design and Construction of Towing Tank Models", Apr. 1980, pp. 50–60, Proceedings of 17th Numerical Control Society Annual Meeting.

Morris: "Robotic Control Systems": More than Simply Collections of ServoLoops, May 1984, pp. 74–79, Control Engineering, V. 31, No. 5.

Primary Examiner—Allen MacDonald
Attorney, Agent, or Firm—Kenyon & Kenyon

[57] ABSTRACT

An ultrasonic scanning system for testing large curved components of fiber/resin matrix composite material, the system ultrasonically testing these components with water jet probes caliper-mounted on the working arm of an industrial robot. The computer reads CAD data appertaining to the component, transfers it to robot-compatible form and delivers it on demand to the robot computer. The computer also reads the data output from the probe and reconciles it with the CAD data to yield as an output a quality map of the component. Instantaneous probe position on the surface of the work piece is computed from data on the starting position of the scanning movement of the probe, and the scanning velocity of the probe.

13 Claims, 4 Drawing Sheets

ULTRASONIC SCANNING SYSTEM

The present invention relates to ultrasonic scanning systems for non-destructive testing of structures.

Ultrasonic scanning of fibre/resin matrix composite components has become the currently accepted non-destructive testing technique adopted by aerospace companies to test large area components made from these new materials.

The ultrasonic technique involves the transmission of an ultrasonic signal in the frequency range 1 MHz–25 MHz through the component thickness and measurement of the attenuation to establish the level of defects present. Such defects may take the form of a delamination between the constituent plies of the component or a collection of microscopic gas voids or bubbles within the matrix. A delamination, in presenting a gas/solid interface, will cause significant attenuation whilst tests have shown that voids or porosity up to approximately 10% cause attenuation in direct proportion to the amount of porosity. Accordingly, the amount of this attenuation is a clear indicator of component quality.

An ultrasonic scanning system of general suitability incorporates a pair of ultrasonic probes (i.e. a transmitter and receiver) immersed in water or embodied in water jet nozzles, the probes being mounted in a device which locates them in correct relation to one another and to the workpiece. The system scans the workpiece in a laced pattern so that its entire surface is systematically examined. There is provision for making a permanent record of the measured attenuation.

The present Applicants have used a so-called flat bed scanning system to scan essentially flat components or those with relatively little curvature, e.g. an aircraft wing skin panel. Their system embodies vertically opposed jet nozzle probes located in adjustable mountings on two roller-supported trolleys which are in turn seated on upper and lower sets of rails laid transversely across a horizontal carriage. The carriage is itself roller mounted on a pair of rails located along the longer sides of a rectangular water tank. The system has the ability to scan or index along the length of the tank i.e. The 'x' direction or scan or index across the tank i.e. in the 'y' direction. The upper probe has a vertical indexing capability, for bringing the probes closer together during a scanning operation, or for indexing if a single probe in an immersed probe scanning mode is to be used on the end of an extended 'z' arm.

Scanning and indexing is achieved by microprocessor-controlled stepper motor drives. The workpiece to be scanned is supported between the probes, and the operator adjusts the ultrasonic and scanning settings as required, the latter on an interactive basis through a visual display unit (V.D.U.) and keyboard. Four levels of quality are determined by a level-calibrating unit and then recorded by a chart recorder.

The stylus of the recorder is linked mechanically to the scanning probe system in the 'x' direction, and the 'y' axis of the recorder is stepper motor driven and linked electrically to the 'y' or 'z' axis of the scanner as required.

U.S. Pat. No. 3,898,838 discloses an ultrasonic scanning system wherein the position of a transducer is adjusted by stepping motors actuated according to signals generated by the transducer for positioning the transducer adjacent and perpendicular to the surface of the article under test. The possibility of a system in which the transducer is positioned by a programmed computer is dismissed as difficult to provide, time-consuming and expensive when irregularly shaped workpieces need to be tested.

U.S. Pat. No. 4,463,609 discloses an ultrasonic scanning system for welded steel offshore structures in which a probe on a mechanical limb is caused to follow a weld bead by feed-back signals from the transducer. EP-A No. 2-0060952 discloses a similar system.

U.S. Pat. No. 4,370,889 discloses an ultrasonic probe mounted on a manipulator for following automatically a predetermined path over the surface of an article under test, augmented with a hand-operated guide element for manually-controlled movement of the probe for detailed exploration when the automatic scanning indicates the possibility of a fault.

In late 1981, Applicants embarked on the design and manufacture of nose cowls for a customer's RB211-535 E4 aircraft engine pods. An extensive composite materials development programme, well advanced at this time, had demonstrated the feasibility of using carbon fibre resin matrix composite materials for much of the construction. Applicants and their customer decided that the new project was ideal for exploitation of the newly acquired composite materials technology. Accordingly, the outer cowl panels which represent a substantial amount of the manufacturing and weight content were designed in composite, with two 180° segments forming the outer surface of the nose cowl.

The testing of early production RB211-535 E4 cowl panels revealed a problem, in that it required approximately 20 hours per component of testing on an adapted flat bed ultrasonic scanner, and it was necessary for the testing to be monitored manually throughout the duration of the test.

Investigations were therefore put in hand to find a more economical scanning system.

According to a first aspect of the present invention there is provided a method of performing a non-destructive testing operation on a workpiece wherein a testing probe is used to scan a surface of the workpiece, the method being characterised by the steps of:

i. mounting the probe on the working end of an arm of an industrial robot;

ii. mounting the workpiece adjacent the robot in a jig so that its position relative to the robot is determined;

iii. inputting the robot with such design data relating to the shape of the workpiece as will enable the robot to move the probe over the said surface of the workpiece;

iv. programming the robot to move the probe in a scanning path across the said surface from a start point to a stop point, through a plurality of continue points, at a predetermined velocity;

v. inputting a computer with test data relating to the shape of the workpiece, the location of the start point on the surface of the workpiece, the said predetermined velocity, the instant of departure of the probe from the start point along the scanning path, and a signal representative of the output from the probe; and vi. running a quality mapping program on the computer, for processing said test data to compute the position of the probe on the surface of the workpiece and provide as output a quality map of the, which displays the position on the surface of the workpiece of zones of different quality within the material from which the testpiece is formed.

According to a second aspect of the present invention, there is provided apparatus for the non-destructive testing of a workpiece, including a testing probe to be scanned over the surface of the workpiece, mechanical means to scan the probe and display means to generate a display representative of the output of the probe; characterised by i. an industrial robot, the arm of which carries the probe, the robot being programmed to move the probe in a scanning path across the surface of the workpiece from a start point to a stop point through a plurality of continue points at a predetermined velocity;

ii. a jig for the workpiece adjacent the robot for determining the position of the workpiece relative to the robot;

iii. a computer for inputting the robot with such design data relating to the shape of the workpiece as will enable the robot to move over the said surface of the workpiece, and for running a quality mapping program which processes test data relating to the shape of the workpiece, the location of the start point on the surface of the workpiece, the said predetermined velocity, the instant of departure of the probe from the start point along the scanning path, and a signal representative of the output from the probe, to provide as output a quality map of which displays the position on the surface of the workpiece of zones of different quality within the material from which the workpiece is formed.

The invention utilises the flexibility of a robotic system. The required accuracy and smoothness of movement of the robot arm is achieved by use of computer aided design (CAD) data appertaining to the workpiece as the data on which the robot relies for its movement commands. In this connection, a translation of co-ordinates is usually necessary, from those of the CAD computer to those required by the computer of the robot.

A major problem in the proposal was how to relate the probe output signal to probe position on the workpiece for the generation of the quality map. Mechanical solutions were investigated but it was then recognised that if the probe is moving at known velocity over the workpiece from a start point of known position, the current position of the probe is determinable from a knowledge of the start point and velocity. Conveniently, the velocity is held constant, and the output signal from the probe is sampled at regular intervals, thereby to build up the required quality map progressively, for as much of the workpiece surface as is required.

The quality mapping program preferably utilises for the production of the quality map test data in the form of a probe position file, which file relates the position at which every sample reading is taken to a matrix which is a two dimensional representation of the surface of the component.

For a better understanding of the invention, and to show more clearly how the same may be carried into effect, reference will now be made, by way of example, to the accompanying drawings, in which.

Figure 1:
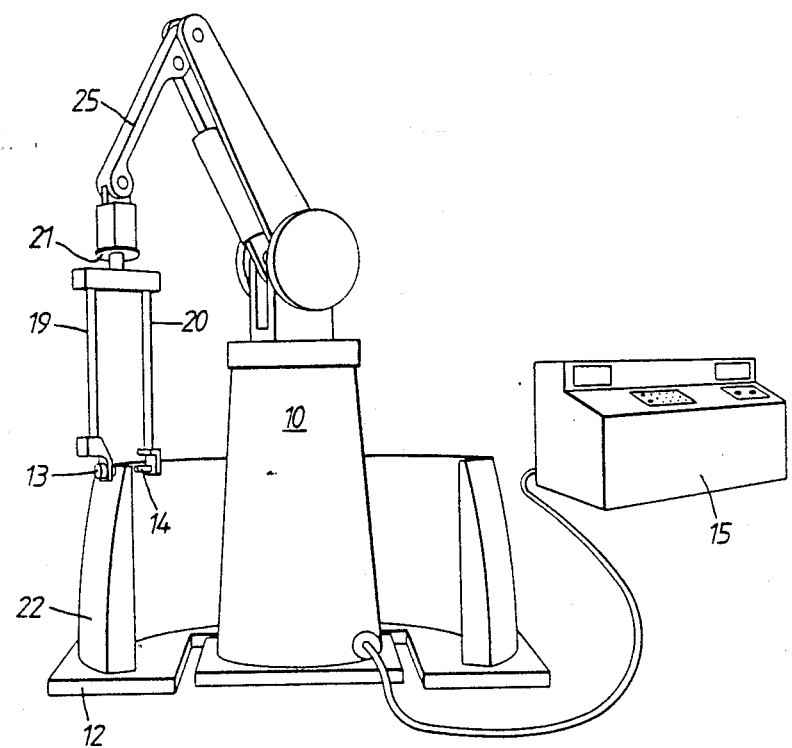
FIG. 1 is an illustration of an ultrasonic scanning system according to the invention being used to scan a cowl panel.
Figure 2:
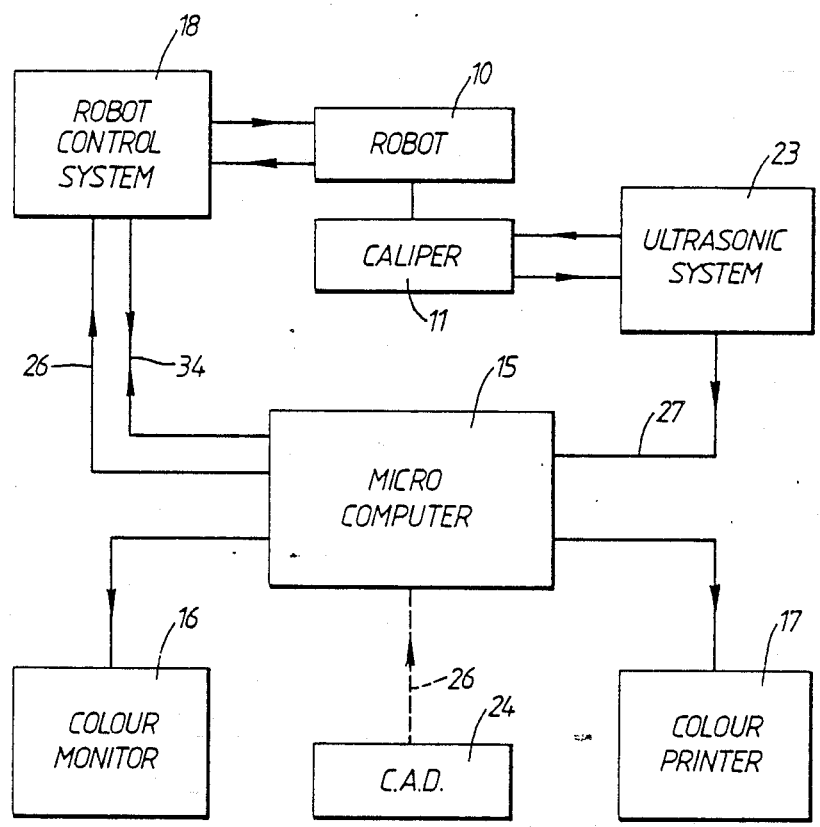
FIG. 2 is a block diagram of components of the ultrasonic scanning system shown in FIG. 1.

Referring to FIGS. 1 and 2 of the drawings, the scanning system comprises the following equipment:
(i) A Cincinnati Milacron T3-566 industrial robot 10.
(ii) Caliper 11 for adjustable water jets and ultrasonic transducers.
(iii) Support jig and water catchment tank 12.
(iv) Caliper-mounted ultrasonic probes 13 and 14.
(v) A Hewlett Packard 9836C microcomputer 15 with colour monitor 16, printer, A3 colour plotter 17, Winchester disc and 3497A Data Acquisition Unit.

The Cincinnati T3-566 robot 10 is a standard, medium size, six axis industrial robot with hydraulic actuation. It has a lifting capacity of 45 kg and is capable of speeds up to 127 cm s$^{-1}$. It has a control system 18 which can be programmed using a teach pendant, a built in keyboard or an external computer via an RS232 serial link using Digital Data Communication Message Protocol (DDCMP).

The workpiece 22 is held in the jig 12 in such a way that it 'wraps around' the robot 10. The base of the jig forms a shallow water reservoir and catchment tank and adjustable locating points (not shown) ensure reliably repeatable positioning of the jig in relation to the robot. Retractable castors (not shown) enable the jig to be removed quickly from the robot's operating area to allow other work to take place.

A small perspex window (not shown) is mounted in the support structure at one end of the jig, providing a calibration point for the ultrasonic system. Perspex is chosen because of its homogeneity and acoustic similarity to carbon fibre reinforced plastics materials.

The caliper 11, which carries an ultrasonic transducer and water jet 13 and 14 at the end of each arm, 19 and 20 respectively, is bolted to the robot's tool face 21. The caliper 11 is light-weight, non-corroding and rigid and serves to damp unwanted vibrations induced by the robot arm 25.

The ultrasonic units 13 and 14 can be adjusted on the arms 19 and 20 of the caliper 11 in order that their jets are perpendicular to the surface of the workpiece 22.

The outputs of the probes 13 and 14 are fed to an ultrasonics package 23 known per se and supplied by Meccasonics Ltd. The output of the package is made compatible with the data acquisition unit of the microcomputer 15, which it inputs.

The microcomputer system 15:
(i) accepts data 24 which defines the geometry of the component, and processes it into robot-compatible form;
(ii) downloads 26 this data progressively to the robot as the scanning operation proceeds;
(iii) acquires 27 data from the ultrasonics package 23, presents it 28 in recognisable form on a screen 16 and stores it 29 for subsequent plotting on a colour plotter or printer 17.

A scanning pattern in robot-compatible form is derivable as follows from the computer-aided design (CAD) data which describes the profile of the workpiece.

The robot arm 25 can be positioned at any point within its working envelope by specifying, relative to a fixed datum, the X, Y and Z co-ordinates of its so-called "tool centre point". In addition, a set of three angular co-ordinates, D the angle of pitch, E the angle of yaw and R the angle of roll, define the orientation of the tool face at this point. The angles are measured relative to the X, Y and Z axes and are therefore independent of the robot arm configuration. In certain situations the definition of five of these axes is sufficient to maintain an ultrasonic prob robot arm perpendicular to the surface of the workpiece.

Figure 3:
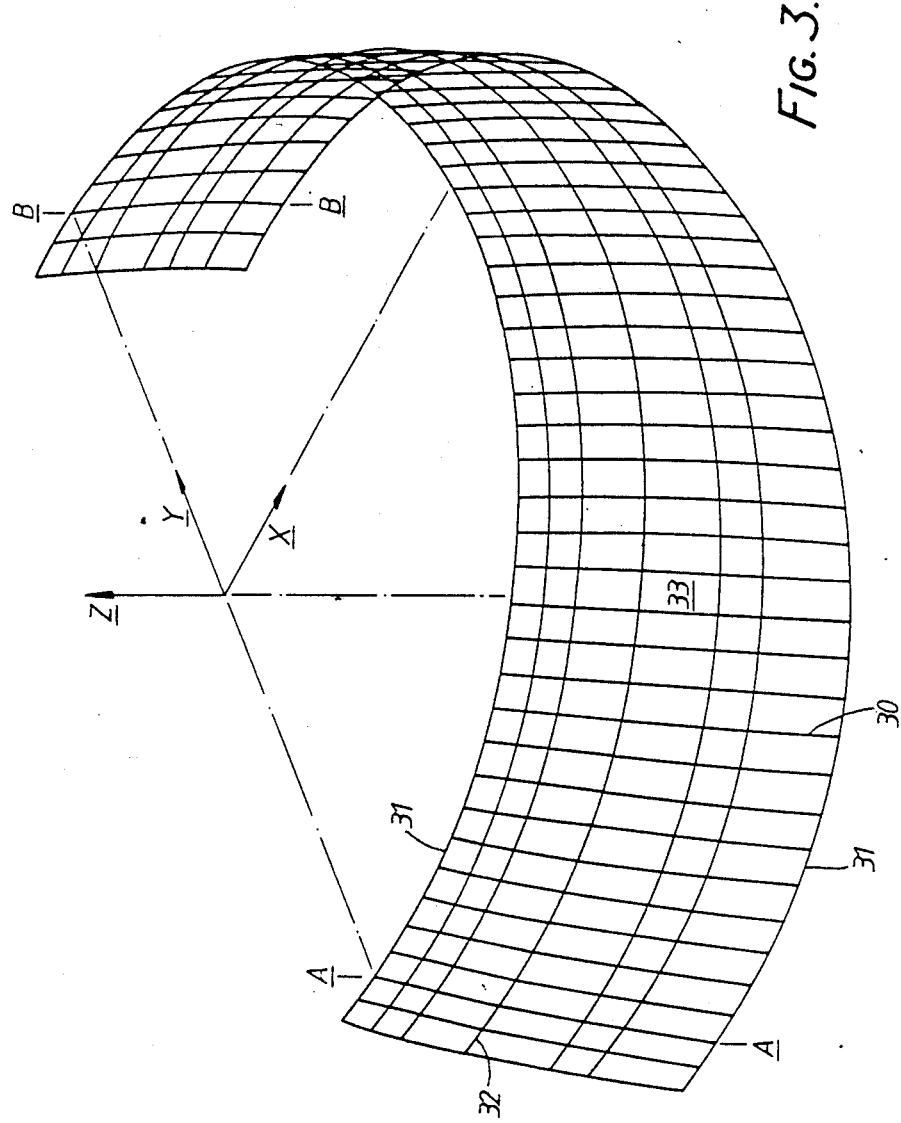
FIG. 3 is a diagrammatic representation of the surface of the cowl panel shown in FIG. 1, generated by the CAD data employed in the manufacture of the cowl panel.

Programming a robot in a CAD/CAM (computer-aided manufacture) environment is analogous to programming an NC (numerically controlled) machine tool. The first stage is to define geometrically the surface of the component. For convenience X, Y and Z axes for defining the surface are chosen to be coincident with the X, Y and Z axes of the robot. In one case of a half cowl profile, as shown in FIG. 3, definition within the CAD system is by 37 radials 30 each made of up to 300 points. Planar cuts 31 are made across the radials to define the forward and aft boundaries of the cowl and the truncated radials obtained are used to construct circumferential curves 32 at selected intervals. The curves so constructed define fully the complex double curvature of the cowl panel, and provide guide lines for the generation of an NC machine toolpath. The curves taken together, provide a computer-generated surface 33, as shown in FIG. 3. The surface extends beyond the real ends A—A and B—B of the workpiece by 200 mm to provide acceleration/deceleration areas for the moving arm of the robot.

The NC software package of the CAD system 24 is used to specify a 5-axis toolpath on the surface 33. To obtain the desired scanning pattern and pitch, the scanning operation is likened to a milling machine cutting in a laced pattern with a 3 mm cutter. The system is programmed to output data points spaced at 100 mm intervals, each point being defined by six co-ordinates; the cartesian co-ordinates X, Y and Z defining a point in space and direction cosines A, B, C, the orientation of a line perpendicular to the surface at that point. The former are directly usable by the robot but not the latter, which still require conversion to robot format.

The resultant file of data points, containing some 70,000 sets of co-ordinates, is transferred as ASCII characters to the microcomputer 15 using a serial link 26 and stored on one floppy disc. As transfer takes place the computer compacts the data, converts it to integer form and checks it for errors to ensure that it is suitable for presentation to the robot control system 18.

When an actual component is to be tested, the computer 15 executes the main program of the system. Briefly, the program handles the manipulation of the CAD co-ordinate data to suit the robot control system 18, which then actuates the movement of the robot using this data. The computer 15 gathers, processes, stores and displays on screen 16 and plotter 17 the results of the scan.

The co-ordinate data CAD file of the workpiece component, taken from the CAD system and stored on a floppy disc as described previously, is processed by the computer 15 to form two files; a robot co-ordinate file and a position look-up table. The robot co-ordinate file contains a transformation of the data from the CAD axes system to the robot axes system. The look-up table is generated by examining the position of every sample point and identifying for it a corresponding position on a matrix which is a two dimensional representation of the surface of the component. The formation of these two files is required only when there is a fresh transfer of data from the CAD system i.e. when a component is to be tested which is of a design not previously known to the microcomputer.

Before scanning can commence, a software communications link 34 must be established between the computer 15 and the robot control system 18. A series of messages, defined by DDCMP, passes between the computer 15 and the robot control system 18, and the successful completion of this sequence indicates that a link exists. After linking, the robot arm 25 is caused to move to an ultrasonic calibration station and is disabled so that the operator can safely approach it to adjust the alignment of the water jets. Once the best jet alignment has been achieved, giving a maximum signal with low noise, a voltage-decibel calibration is taken. This is used during testing to convert the incoming ultrasonic signal to attenuation values in decibels.

By performing at this stage a decibel-level calibration, ultrasonic data can be presented in colour, with different colours representing different bands of attenuation. The level calibration defines the decibel range each colour will represent. If the data is stored in decibel form, re-calibration can take place whenever desired. Conveniently eight colours are used.

Figure 4:
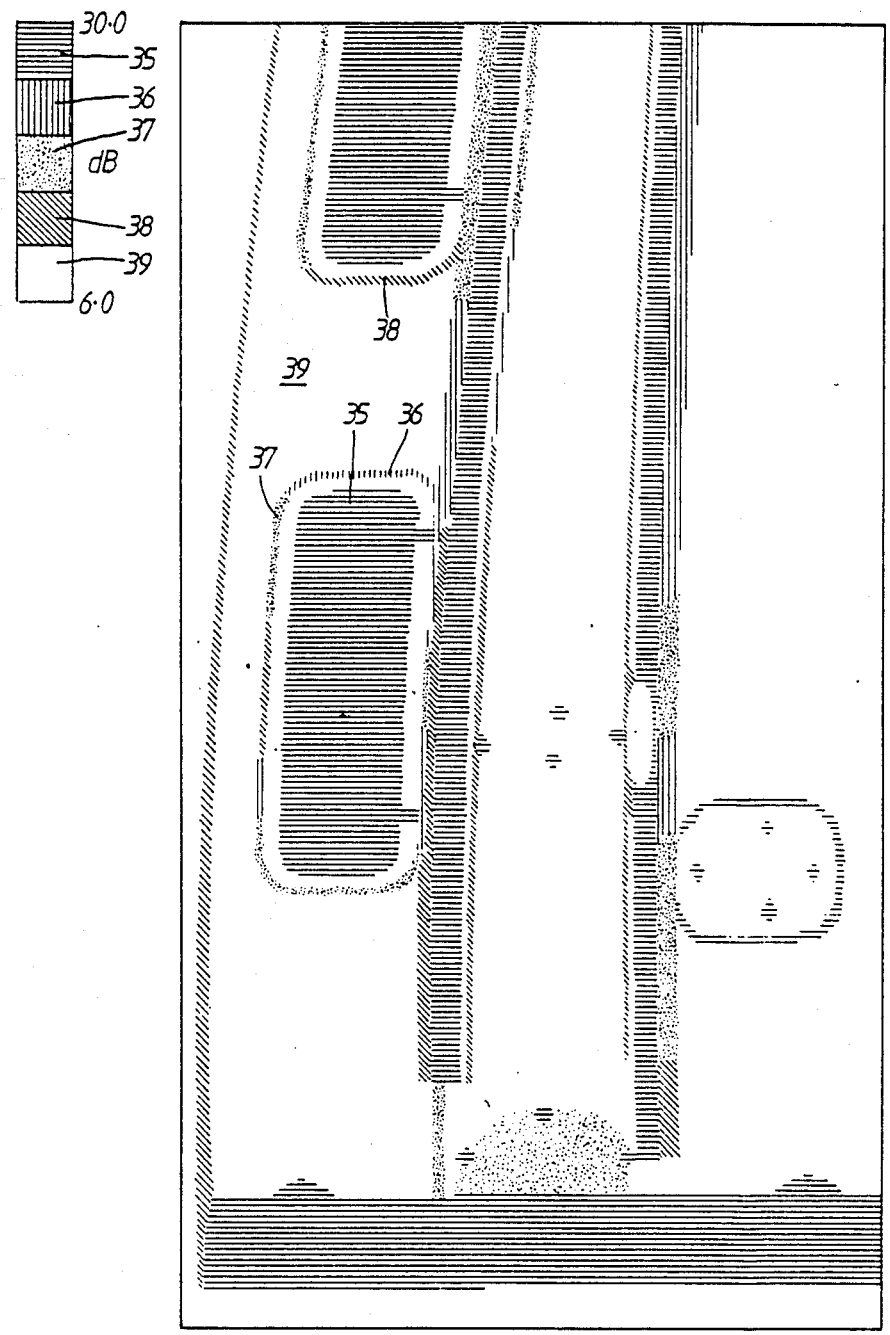
FIG. 4 is an illustration of a two dimensional display of the quality of a component under test using the scanning system according to the invention.

In FIG. 4 such a coloured quantity map is represented schematically, by different shading. Apertures in the workpiece appear in the coloured map as black areas 35. Areas on the map are in fact made up of a multitude of spaced, coloured dots, each representing one sampled probe output signal. It is usual for each area to have a predominating colour, for example, red 36, yellow 37 and green 38, with white 39 for areas of least attenuation, but to include occasional dots of other colours, and skilled readers will appreciate that this is not brought out in FIG. 4. Nevertheless, they will recognise the shape of the component and the value of the map, and will appreciate the importance of experience and judgement in the interpretation of the maps in day-to-day use of the invention.

The velocity at which the probe moves over the workpiece is conveniently within a range of from 2.5 cm s$^{-1}$ to 33 cm s$^{-1}$, the preferred standard speed being 25 cm s$^{-1}$. Scanning may be uni-directional or bi-directional, the former giving slightly greater accuracy in the positioning of probe output sample signals within the matrix, which results in a more sharply defined quality map.

When the operator elects to start scanning, the robot control 18 is sent a sequence of co-ordinates to take it from the calibration point to the start of the first line 32 to be scanned. The computer then extracts the appropriate line from the robot co-ordinate file, and constructs a data sequence which includes the robot speed and function at each point in the sequence for sending to the robot.

The two computers are synchronised by providing for the robot computer 18 to wait until a signal to start a scanning sequence is received from the external computer 15. After receiving the start signal, the robot computer 18 requests the data for the next scanning sequence and this is sent from the external computer 15. The robot computer 18 starts to execute the sequence, and the external computer 15 waits for a synchronisation pulse from the robot computer 18 which signifies that the robot has completed the acceleration phase of the sequence and is now at constant velocity. The external computer 15 starts to sample the ultrasonic signal. Conveniently, the sampling rate changes with the chosen robot speed, such that a sample is taken every 3 mm along the scan line 32. When a sample probe signal is taken, the computer reads a voltage, converts the reading into a decibel value, uses the look-up table to store the decibel value at the appropriate position in the matrix and draws the representative colour on the screen. This process is repeated at up to 100 times a second, depending on the robot speed.

Scanning will normally proceed until the whole component has been scanned but it is convenient to provide that the operator can stop the scan at any time to change the scan pattern or re-calibrate. For a typical workpiece, a complete bi-directional scan at a speed of 25 cm $s^{-1}$, during which over 350,000 samples are processed, displayed and stored, had a duration of 85 minutes.

Scanning of left- and right-hand components from one CAD file can be accomplished by using the computer 15 to mirror the data about the X-Z plane. In this mode each sequence is mirrored prior to down-loading to the robot computer 18.

The quality map of the component gradually builds up, and may be shown on the screen 16, as the scan progresses. Thus, the component can be inspected as scanning takes place, although a full inspection can take place only after the scan is complete. Conveniently, up to four scans can be stored at a time and any one of them can be selected subsequently for inspection. The operator can choose to view the whole component on the screen at 1/20th scale or part of it at between 1/6th and full scale. Other options allow plotting of the complete component at ¼ scale or small section at full scale.

The system developed offers many advantages over a flat-bed system and indeed over any non-robotised system. The robot gives the dexterity needed to scan very highly curved components and the use of CAD data gives flexibility in the variety of shapes that can be scanned. The positioning and timing of the robot have proven repeatable, resulting in very accurate and clear ultrasonic records. The system can easily be used by a single operator who needs little expertise in the use of computers or robots.

Contemplated developments of the system described with reference to the drawings include; replacement of the T3-566 robot 10 with an electric robot, which should make faster scanning speeds feasible; a modified CAD link 26 to allow the 9836C computer 15 to act as a terminal of the central computer of the CAD system on which the robot relies; and new jet configurations to enable inspection of any areas in components of complex shape which are not accessible to the opposed probe configuration illustrated herein. Meccasonics Limited, mentioned above, has a business address at Ross-on-the-Wye, England. The Cincinnati-Milacron robot originated from Cincinnati-Milacron, Ohio, U.S.A. and the Hewlett-Packard microcomputer originated from Hewlett-Packard Corporation in California, U.S.A.

While testing probes which are not ultrasonics probes are contemplated, and probes which do not comprise separate transmitter and receiver heads which face one another, Applicants see the major use of the invention, at least in the immediate future, as being with separate transmitter and receiver heads which face one another through the thickness of the workpiece.

We claim:

1. A method of performing a non-destructive testing operation on a workpiece, wherein a testing probe is used to scan a surface of the workpiece, the method being characterized by the steps of:
   i. mounting the probe on the working end of an arm of an identical robot having a controller;
   ii. mounting the workpiece adjacent the robot in a jig so that its position relative to the robot is determined;
   iii. providing the controller of the robot with such design data relating to the shape of the workpiece as will enable the robot to move the probe over the surface of the workpiece;
   iv. programming the controller to command the robot to move the probe in a scanning path across the surface of the workpiece from a start point to a stop point, through a plurality of continue points, at a predetermined velocity;
   v. inputting a computer with test data relating to the shape of the workpiece, the location of the start point on the surface of the workpiece, the predetermined velocity of probe movement, the instant of departure of the probe from the start point along the scanning path, and a signal representative of the output from the probe; and
   vi. running a quality mapping program on the computer, for processing said test data to compute based solely upon said start point, said predetermined velocity, and said instant of departure without any feedback of position data the position of the probe on the surface of the workpiece which displays the position on the surface of the workpiece of zones of different quality within the material from which the workpiece is formed.

2. A method according to claim 1 characterized in that the step of providing the controller of the robot with the design data is performed by said computer.

3. A method according to claim 1 or 2 characterized in that the predetermined velocity of probe movement is a constant velocity.

4. A method according to claim 3 characterized in that the quality mapping program is such as to provide a quality map in which zones of different quality within the workpiece are distinguished on the map as zones of different color.

5. A method according to claim 4 characterized in that the testing operation is an ultrasonic testing operation and the testing probe is an ultrasonic probe.

6. A method according to claim 3 characterized in that the testing operation is an ultrasonic testing operation and the testing probe is an ultrasonic probe.

7. A method according to claim 2, characterized in that the testing operation is an ultrasonic testing operation and the testing probe is an ultrasonic probe.

8. A method according to claim characterized in that the testing operation is an ultrasonic testing operation and the testing probe is an ultrasonic probe.

9. A method according to claim 1 or 2 characterized in that the quality mapping program is such as to provide a quality map in which zones of different quality within the workpiece are distinguished on the map as zones of different color.

10. A method according to claim 9 characterized in that the testing operation is an ultrasonic testing operation and the testing probe is an ultrasonic probe.

11. Apparatus for the non-destructive testing of a workpiece, including a testing probe to be scanned over a surface of the workpiece, mechanical means to scan the probe and display means to generate a display representative of the output of the probe; characterized by
   i. The mechanical means comprising an industrial robot having an arm which carries the probe and a controller for moving the arm, the controller being programmed to move the probe in a scanning path across the surface of the workpiece from a start point to a stop point through a plurality of continue points at a predetermined velocity;

ii. a jig for the workpiece adjacent the robot for determining the position of the workpiece relative to the robot;

iii. a computer for inputting the robot controller with such test data relating to the shape of the workpiece as will enable the controller to command the robot to move the probe over the surface of the workpiece, and for running a quality mapping program which processes test data to compute, based solely upon the location of the start point on the surface of the workpiece, the predetermined velocity of probe movement, the instant of departure of the probe from the start point along the scanning path, and a signal representative of the output from the probe without any feedback of position data, to provide as output to the display means a quality map of the workpiece of zones of different quality within the material from which the workpiece is formed.

12. Apparatus as claimed in claim 11 characterized in that the testing probe is an ultrasonic testing probe.

13. Apparatus as claimed in claim 11 or 12 for testing a workpiece which has a small thickness relative to its width and length, and characterized by a testing probe which comprises a transmitting probe for addressing one major surface of the workpiece and a receiving probe for addressing the other major surface, the said probes being mounted in opposition to each other, one on each arm of a caliper carried by the arm of the robot.

* * * * *

UNITED STATES PATENT AND TRADEMARK OFFICE
CERTIFICATE OF CORRECTION

PATENT NO. : 4,881,177
DATED      : 14 November 1989
INVENTOR(S) : James Harvey McClean, et al.

It is certified that error appears in the above-identified patent and that said Letters Patent is hereby corrected as shown below:

Column 2, line 63, change:  "the," to --the workpiece--.

Column 3, line 25, change:  "of which" to --of the workpiece which--.

Column 5, line 4, change:  "prob" to --probe on the--.

Column 7, line 68, change:  "identical" to --industrial--.

Signed and Sealed this

Eighth Day of January, 1991

Attest:

HARRY F. MANBECK, JR.

*Attesting Officer*   *Commissioner of Patents and Trademarks*